June 13, 1950 M. P. H. LEENDERS Plant Pat. 950
ROSE PLANT
Filed May 5, 1949
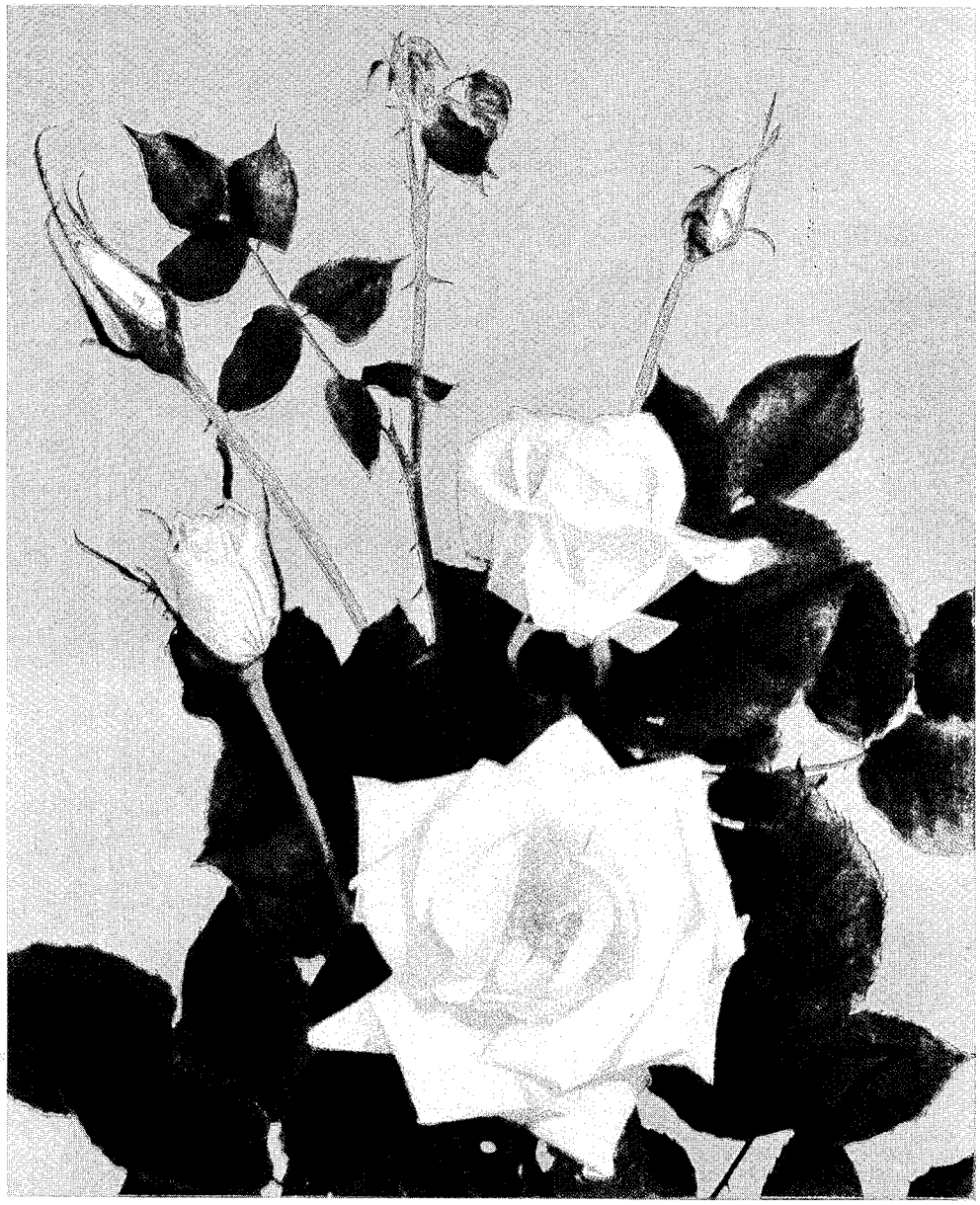
Inventor
M. P. H. Leenders
By Robb & Robb
Attorneys

UNITED STATES PATENT OFFICE

950

ROSE PLANT

Mathieu P. H. Leenders, Steyl-Tegelen, Netherlands, assignor to Jackson & Perkins Company, Newark, N. Y., a corporation of New York Application May 5, 1949, Serial No. 91,613

1 Claim. (Cl. 47—61)

The present invention relates to a new and distinct variety of rose plant, the origination of which had for its primary object the production of a variety having the outstanding color and fragrance of its seed parent "Vanessa" but which would improve its characteristic lack of strength and failure to produce a satisfactory quantity of blooms.

"Vanessa" was selected because it had a very desirable background, involving a series of crossings with "Talisman," "Ophelia" and "Souvenir de Claudius," but was otherwise unsatisfactory, as above stated. (All four of these varieties are unpatented.)

However, by crossing it with "Burgemeester van Oppen," I obtained this new variety which is characterized as to novelty by the combination of: its heavy fruity fragrance, long lasting and tending to permeate all its surroundings; its branching habit which gives great production of medium length stems and flowers in the greenhouse, making it particularly desirable for cut flower purposes; and, lastly, its attractive yellow color, all as hereinafter more specifically set forth.

Asexual reproduction of this new variety shows the foregoing characteristics come true to form and are established.

The accompanying drawing illustrates specimens of this new variety at different stages of development of the flowers from bud to full-blown blooms with a background of its dark green foliage.

The following is a detailed description of the new variety, color terminology being in accordance with Ridgway's Color Standards and Nomenclature:

Parentage: Seedling.
- *Seed parent.*—"Vanessa" (unpatented).
- *Pollen parent.*—"Burgemeester van Oppen" (unpatented).

Classification: Botanic and commercial—hybrid tea.

Place where asexually reproduced: Newark, New York.

Method of reproduction: By budding.

*Flower*

(The following observations made in greenhouse at Newark, New York, in the morning in the month of December.)

Blooming habit: Recurrent—continuous.

Bud:
- *Size.*—Large.
- *Form.*—Pointed. Is not affected by wet or hot weather.

- *Color.*—When sepals first divide—Orange, Plate 3. When petals begin to unfurl—Capucine Orange, Plate 3. When half blown—inside of petals—Light Cadmium, Plate 4; reverse of petals—Deep Chrome, Plate 3.
- *Sepals.*—Branched, "hood" above bud. Curl back when petals begin to unfurl. Color—inside—Pale Veronese Green, Plate 18; outside—Light Bice Green, Plate 17.
- *Calyx.*—Shape—apple. Size—large. Aspect—smooth. Odor when rubbed—none. Color—Scheele's Green, Plate 6.
- *Peduncle.*—Length—long. Aspect—smooth. Color—Lettuce Green, Plate 5. Strength—stiff; slender.
- *Opening.*—Bud opens up well.

Bloom:
- *Size.*—Large. Average size when fully expanded, 5".
- *Borne.*—Singly.
- *Stems.*—Medium length; normal strength.
- *Form.*—When first open—high center. Permanence—retains its form to the end.
- *Petalage.*—Double (full but open center). Number of petals under normal conditions, 25.
- *Color.*—Center of flower—Orange Buff, Plate 3. Outer petals—Buff Yellow, Plate 4, outer edges lightly overcast with Shrimp Pink, Plate 1. Base of petals (aiglet)—Lemon Chrome, Plate 4. Inside of petals—Light Orange Yellow, Plate 3. Reverse of petals—Apricot Yellow, Plate 4. General tonality from a distance—Orange Buff, Plate 3.
- *Discoloration.*—General tonality at end of first day—Orange Buff, Plate 3. Second day—Orange Buff, Plate 3, to Pale Orange Yellow, Plate 3. Third day—Maize Yellow, Plate 4, overcast with Shrimp Pink, Plate 1.

Petals:
- *Texture.*—Thick. Is not affected by wet or hot weather.
- *Appearance.* — Inside — satiny; outside—shiny.
- *Form.*—Oval.
- *Arrangement.*—Informal (with "rags" in center). Petaloids in center—few; small.
- *Persistence.*—Drop off cleanly.
- *Fragrance.*—Strong and long lasting. Nature—heavy fruity fragrance.
- *Lasting quality.*—On the plant and as cut flower—very long.

Genital organs:

*Stamens, anthers.*—Medium size; many. Color—Light Orange Yellow, Plate 3.

*Stamens, filaments (threads).*—Long. Color—Capucine Orange, Plate 3.

*Pollen.*—Color—Pale Yellow Orange, Plate 3.

*Styles.*—Columnar; uneven length; short; thin.

*Stigmas.*—Color—Baryta Yellow, Plate 4.

*Ovaries.*—All enclosed in calyx.

*Plant*

Form: Bush.

Growth: Vigorous; branching.

Foliage: 5 to 7 leaflets.

*Size.*—Medium.

*Quantity.*—Abundant.

*Color.*—New foliage: upper side—Oil Green, Plate 5, with overcast of Oxblood Red, Plate 1, and serrations Oxblood Red, Plate 1; under side—Yellowish Oil Green, Plate 5, with overcast of Oxblood Red, Plate 1, and serrations Oxblood Red, Plate 1. Old foliage: upper side—Forest Green, Plate 17; under side—Light Bice Green, Plate 17.

*Shape.*—Oval pointed.

*Texture.*—Upper side — leathery; smooth. Under side—smooth. Ribs and veins—Ordinary.

*Edge.*—Serrated (saw toothed).

*Serrations.*—Single; small.

*Lear stem.*—Color—Absinthe Green, Plate 31. Under side—smooth.

*Stipules.*—Medium length; smooth.

*Disease resistance.*—Resistant.

Wood:

*New wood.*—Color—Lettuce Green, Plate 5. Bark—smooth.

*Old wood.*—Color—Spinach Green, Plate 5. Bark—smooth.

Thorns:

*Thorns.*—Quantity—on main stalks from base and on laterals from stalk—ordinary. Form—narrow base; medium length; hooked downward. Color when young—Dark Vinaceous, Plate 27. Position—irregular.

*Prickles and short needles.*—None.

I claim:

A new and distinct variety of rose plant characterized as to novelty by its strong, long lasting and penetrating fragrance; by its prolific branching habit and heavy production of flowers particularly suitable for cut flowers; and by its attractive yellow blooms, substantially as shown and described.

MATHIEU P. H. LEENDERS.

No references cited.